United States Patent [19]
Baumeister et al.

[11] Patent Number: 5,877,340
[45] Date of Patent: Mar. 2, 1999

[54] PROCESS FOR THE PREPARATION OF SUBSTITUTED AROMATIC AMINO COMPOUNDS

[75] Inventors: Peter Baumeister, Flüh; Urs Siegrist, Eiken, both of Switzerland

[73] Assignee: Novartis Consumer Health S.A., Nyon, Switzerland

[21] Appl. No.: 930,297

[22] PCT Filed: May 6, 1996

[86] PCT No.: PCT/EP96/01876

§ 371 Date: Oct. 1, 1997

§ 102(e) Date: Oct. 1, 1997

[87] PCT Pub. No.: WO96/36588

PCT Pub. Date: Nov. 21, 1996

[30] Foreign Application Priority Data

May 18, 1995 [CH] Switzerland .............................. 1477/95

[51] Int. Cl.$^6$ ................................................. C07C 209/38
[52] U.S. Cl. .......................... 558/418; 564/253; 564/261; 564/265; 564/417
[58] Field of Search ................. 564/417, 265, 564/261, 253; 558/418

[56] References Cited

U.S. PATENT DOCUMENTS 3,666,813  5/1972  Hindin et al. ........................... 260/580

FOREIGN PATENT DOCUMENTS

A 2 042 368  4/1971  Germany .
WO95/32941  12/1995  WIPO .

OTHER PUBLICATIONS

J. P. Marino, et al., Synthetic Communications, vol. 24, No. 6, 1994, pp. 839–848.
Rylander, P.N., Hydrogenation Methods, Academic Press, London, 1985, pp. 326–329.
Freifelder, M., Practical Catalytic Hydrogenation, Wiley, New York, 1971, p. 256.
Rylander, P.N., Catalytic Hydrogenation in Organic Synthesis, Academic Press, London, 1979, p. 140.
Freifelder, M., Practical Catalytic Hydrogenation, Wiley, New York, 1971, pp. 305–306.
Rylander, P.N., Hydrogenation Methods, Academic Press, London, 1985, p. 77.

*Primary Examiner*—Brian M. Burn
*Attorney, Agent, or Firm*—William K. Wissing

[57] ABSTRACT

The invention relates to processes for preparing substituted aromatic amino compounds which contain at least one unsaturated —CN bond or carbonyl group on the aromatic radical or in a side chain, by catalytic hydrogenation of appropriate substituted aromatic nitro compounds in the presence of a modified noble metal catalyst of platinum which is modified with a metal selected from lead, mercury, bismuth, germanium, cadmium, arsenic, antimony, silver and gold.

29 Claims, No Drawings

PROCESS FOR THE PREPARATION OF SUBSTITUTED AROMATIC AMINO COMPOUNDS

The present invention relates to a hydrogenation process for the preparation of aromatic amino compounds which contain, directly on the aryl ring or in a side chain, one or more functional groups which can likewise be hydrogenated or eliminated by hydrogenolysis, such as nitrile groups, imino groups, carbonyl groups or halogen. The preparation takes place by catalytic hydrogenation of the corresponding aromatic nitro compounds in the presence of a modified noble metal catalyst. The invention also relates to the use of modified noble metal catalysts for the hydrogenation of aromatic nitro compounds which are substituted by nitrile, imino or carbonyl groups or by halogen.

It is known that aromatic nitro compounds can be reduced in the presence of noble metal catalysts and hydrogen to give aromatic amines, with very good yields. When other hydrogenatable or hydrogenolytically eliminable functional groups are present at the same time, for example nitrile, imino or carbonyl groups or halogen, particular measures must be taken in order to avoid the formation of unwanted by-products, whose separation from the desired product is often highly complex or, in particularly unfavourable cases, totally impossible. A particular problem is posed by selective reduction when two or more hydrogenatable or hydrogenolytically eliminable functional groups are present in one compound.

The prior art includes a number of proposals for the selective reduction of aromatic nitro compounds substituted by functional groups which can be hydrogenated and/or hydrogenolytically eliminated. All of these proposals have the disadvantage that they are suitable only for particular classes of substituted aromatic nitro compounds, and cannot therefore be employed universally. Moreover, the reaction solutions usually comprise additional components which after the reaction must, in some cases with considerable effort, be separated off and disposed of.

For instance, JP-62 123 162 proposes carrying out hydrogenation with Raney-nickel in the presence of cyanamide or dicyandiamide.

Hungarian Patent Application HU 207 713B describes a process in which 2,3-dichloro-6-nitrobenzonitrile is hydrogenated to the corresponding aniline using a Pd/C catalyst in the presence of concentrated HCl.

In another process, which is described in DE-A-37 03 236, nitrobenzaldoxime O-ethers are reduced directly to the corresponding anilines using Raney nickel.

JO 2009-827-A of 29.3.89 describes the reduction of appropriately substituted nitrobenzyl derivatives to form the corresponding anilines, using Raney nickel in the presence of, for example, melamine derivatives.

Examples of other proposals are the Bechamp reduction of DE-A-2 065 869 or a sulfide reduction, J. Org. Chem. 50, (1985) 5782.

The aim of the present invention is to provide a process, which both economically and ecologically is simple to carry out on the industrial scale, for the hydrogenation of aromatic nitro compounds which are substituted by hydrogenatable or hydrogenolytically eliminable functional groups such as nitrile groups, imino groups, carbonyl groups or halogen.

It has been found that these hydrogenations can be accomplished advantageously if specially modified platinum catalysts are employed. Counter to expectations it has been found that, with these catalysts, aromatic nitro compounds can be reduced selectively to the corresponding amino compounds without at the same time hydrogenating the unsaturated —CN or —CO bonds of the substituents on the aromatic nitro compound.

A further advantage of the process is that it does not give rise to the formation of any Fe muds nor any acidic or sulfur-containing effluents requiring disposal. The product is obtained in high purity and the reaction can be carried out in conventional reactors without the need to use special materials.

The present invention relates to a process for the preparation of substituted aromatic amino compounds containing at least one —CN multiple bond or a carbonyl group on the aromatic radical or in a side chain, by catalytic hydrogenation of appropriate substituted aromatic nitro compounds in the presence of a modified noble metal catalyst, which process comprises the use as noble metal catalyst of platinum which is modified with a metal selected from the group consisting of lead, mercury, bismuth, germanium, cadmium, arsenic, antimony, silver and gold.

Some of the catalysts used in the process according to the invention are new and some of them are already known. DE-A-2 042 368 and J. Mol. Catal. 71, (1992) 317 describe the preparation and use of platinum catalysts modified with tin, lead, germanium, aluminium, zinc, bismuth and silver for the preparation of halogen-substituted aromatic amines.

It has surprisingly been found that, if compounds of iron, ruthenium, cobalt, copper or manganese are used as additional promoters for the lead-, mercury-, bismuth-, germanium-, cadmium-, arsenic-, antimony-, silver- and gold-modified platinum catalysts, the yields in the process according to the invention can be raised further.

The promoters can be either added directly to the reaction mixture as salts or deposited as insoluble compound on the surface of the catalyst in the course of its preparation or modification.

Preferred promoters which can be used in the catalysts are: $Fe^{2+}$, $Fe^{3+}$, $Ru^{3+}$, $Mn^{2+}$ and $Mn^{3+}$ as salts with anions $Cl^-$, $Br^-$, $F^-$, $SO_4^{2-}$, $NO_3^-$, acetate, citrate, gluconate, lactate, oxalate, benzoate, naphthenate, tartrate and formate, or in the form of an appropriate metal complex.

The promoter is preferably used in a quantity of from 0.001 to 10% by weight, based on the aromatic nitro compound employed, with the promoter used being, in particular, an iron salt, very preferably $FeCl_2 \cdot 4H_2O$.

The use of compounds of iron and manganese as promoters for certain platinum catalysts which are able selectively to reduce aromatic nitro compounds to the corresponding amines in the presence of halogen is known, for example, from U.S. Pat. No. 4 212 824 and U.S. Pat. No. 2 823 235.

In addition to the promoters mentioned, the hydrogenation can be accelerated by using a co-promoter. Suitable co-promoters are, in general, ion pairs or salts which are soluble in organic solvents, preferably ionophores which are known from electrochemistry, and in particular as cation $(C_1\text{-}C_6 alkyl)_4 N^+$ or

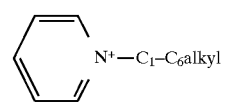

and as anion $Cl^-$, $Br^-$, $F^-$, $BF_4^-$, $PF_6^-$, $NO_3^-$, $F_3CSO_3^-$, $BPh_4^-$, $PhCOO^-$,

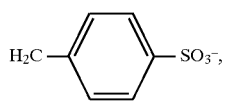

$CH_3SO_3^-$ and $F_3COO^-$. The use of these co-promoters is particularly preferred in the process according to the invention. Very particular preference is given to the use of co-promoters comprising quarternary ammonium bases, especially tetramethylammonium chloride. The co-promoters are preferably used in a quantity of from 0.001 to 10% by weight, based on the aromatic nitro compound employed.

In the process according to the invention the metal modifying the platinum catalyst is preferably lead, in particular in the form of lead acetate, lead nitrate, lead chloride and lead tetraalkyls, for example lead tetraethyl.

The noble metal catalyst is used in particular in a quantity of 0.1 to 5% by weight, based on the aromatic nitro compound employed, with the weight ratio of platinum to the modifying metal being from 1:0.001 to 1:1, preferably from 1:0,1 to 1:0.5.

It is preferred to use a noble metal catalyst containing from 1 to 10% by weight of platinum. The platinum which can be employed for the modification can be used in the form of platinum black, platinum oxide or, preferably, in metallic or oxidized form applied to a support. Particularly suitable supports are active charcoal, silicic acid, silica gel, alumina, calcium carbonate, calcium phosphate, calcium sulfate, barium sulfate, titanium oxide, magnesium oxide, iron oxide, lead oxide, lead sulfate or lead carbonate, particular preference being given to silica gel, alumina or calcium carbonate. Platinum applied to the abovementioned support material is commercially available or can be prepared by methods which are familiar to the person skilled in the art, as are described for example in DE-A-2 042 368.

The process according to the invention is carried out at a pressure of from 1 to 100 bar and at a temperature of from +20° to +160° C., preferably at a pressure of from 20 to 40 bar and at a temperature of from +100° to +140° C.

The choice of the solvent is not critical, which is a particular advantage of the process according to the invention. It is possible to employ solvents of high solvency which are not sufficiently inert in the presence of unmodified platinum catalysts, examples of these solvents being ketones. Preferred solvents are water, alcohols such as methanol, ethanol, n-propanol, isopropanol, n-butanol, the isomeric butanois and cyclohexanol, ethers, esters and ketones, for example diethyl ether, methyl tert-butyl ether, tetrahydrofuran, dioxane, dimethoxyethane, ethyl acetate, butyl acetate, butyrolactone, acetone, methyl ethyl ketone, methyl isobutyl ketone or cyclohexanone, carboxylic acids such as acetic acid and propionic acid, dipolar aprotic solvent such as dimethylformamide, N-methylpyrrolidone, dimethylacetamide, sulfolane, dimethyl sulfoxide or acetonitrile, apolar solvents, such as toluene or xylene, chlorinated aromatic hydrocarbons, such as methylene chloride, $C_3$–$C_7$alkane or cyclohexane.

These solvents can be employed in pure form or as mixtures. In particularly preferred embodiments of the process according to the invention the solvents used are tetrahydrofuran, dimethoxyethane, methyl ethyl ketone, acetone and cyclohexanone in pure form or as mixtures with alcohols and/or $C_1$–$C_4$carboxylic acids.

Examples of compounds with —CN multiple bonds are oximes, imines, isocyanates, isocyanurates, hydrazones, azines and nitriles. They may be either attached directly to the aromatic structure or else be present in a side chain, as substituents. Preferred groups are nitriles, imines, oximes and hydrazones.

Examples of compounds with —CO multiple bonds are ketones, for example aryl alkyl ketones or quinones. The CO bonds can be attached directly to the nitroaromatic compound or can be present in a side chain.

The side chains may be aliphatic, cycloaliphatic, aromatic, heteroaromatic, mixed aliphatic-cycloaliphatic, aromatic-aliphatic or heteroaromatic-aliphatic side chains.

The process is also suitable when —ON multiple bonds and carbonyl groups are present simultaneously as substituents in the overall molecule or in the side chain.

The nitrile, oximino, hydrazone and mine groups or the carbonyl groups are preferably attached directly to the aromatic radical of the aromatic nitro compound or are attached via a pyrazolyl, pyrimidyl, or pyrimidyldione side chain, which can be substituted additionally by oxygen, halogen or $C_1$–$C_4$alkyl.

The aromatic nitro compounds can be substituted by any additional groups desired.

In a preferred embodiment of the process the aromatic nitro compound additionally comprises a halogen substituent on the nitroaromatic radical or in a side chain.

The terms aromatic nitro compounds and amino compounds in the context of the present invention refer to those systems which obey the Hückel 4n+2 electron rule, examples being aromatic hydrocarbons such as benzenes, polycyclic hydrocarbons (including those which are partially hydrogenated, such as tetralin), biphenyls, cyclopentadienyl anion and cycloheptatrienyl anion, anthraquinones, heteroaromatic compounds, such as pyridines, pyrroles, azoles, diazines, triazines, triazoles, furans, thiophenes and oxazoles, condensed aromatic compounds such as naphthalene, anthracene, indoles, quinolines, isoquinolines, carbazoles, purines, phthalazines, benzotriazoles, benzofurans, cinnolines, quinazoles, acridines and benzothiophenes.

The aromatic nitro compounds can contain one or more nitro groups. They preferably contain one or two nitro groups.

A preferred group of compounds are those of the formula I

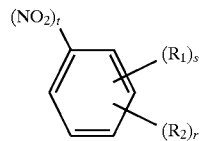

in which
  $R_1$ is a group containing at least one —CN multiple bond or carbonyl function;
  $R_2$ is hydrogen, halogen, $C_1$–$C_{12}$alkyl, $C_1$–$C_{12}$haloalkyl, $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_{12}$hydroxyalkyl, $C_3$–$C_8$cycloalkyl, $C_6$–$C_{16}$aryl, $C_7$–$C_{16}$aralkyl, $C_3$–$C_6$heterocycloalkyl, $C_3$–$C_{16}$heteroaryl, $C_4$–$C_{16}$heteroaralkyl, $X_1R_3$, where $R_3$ is hydrogen, $C_1$–$C_{12}$alkyl, $C_1$–$C_{12}$haloalkyl, $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_{12}$hydroxyalkyl, $C_3$–$C_8$cycloalkyl, $C_6$–$C_{16}$aryl, $C_7$–$C_{16}$aralkyl, $C_3$–$C_6$heterocycloalkyl, $C_3$–$C_{16}$heteroaryl or $C_4$–$C_{16}$heteroaralkyl, $X_1$ is oxygen or sulfur;

r, s and t are 1, 2 or 3, and r+s+t is less than or equal to 6.

In the compound of the formula I r, s und t are preferably 1 or 2.

$R_1$ is preferably a group Q—CN, Q—C=N—$R_4$ or Q—CO$R_5$, where $R_4$ is OH, O—($C_1$–$C_{12}$)alkyl, NHCO ($C_1$–$C_{12}$)alkyl or NHCO phenyl, $R_5$ is $C_1$–$C_{12}$alkyl, O—$C_1$–$C_{12}$alkyl or O—N=C[($C_1$–$C_{12}$)alkyl]$_2$ and Q is either a direct bond is an unsubstituted or halogen- or $C_1$–$C_4$alkyl-substituted pyrazolyl, pyrimidyl, or pyrimidyidione radical.

A further preferred subgroup of compounds of the formula I comprises those in which $R_2$ is hydrogen, halogen, $C_1$–$C_6$alkyl, $C_1$–$C_6$haloalkyl or $C_1$–$C_6$haloalkoxy, preferably hydrogen, halogen, methyl, difluoromethoxy or trifluoromethoxy.

A likewise preferred group of compounds are obtained if Q is a direct bond and $R_1$ is a nitrile group or —C=N—O$R_4$, $R_2$ is halogen and r, s and t are each 1 or 2 and $R_4$ is OH, O—$C_1$–$C_{12}$alkyl, NHCO($C_1$–$C_{12}$)alkyl or NHCO phenyl.

Similarly preferred compounds are those in which Q is a direct bond and $R_1$ is COH or CO($C_1$–$C_{12}$)alkyl.

In the above definitions, halogen is fluorine, chlorine, bromine or iodine, preferably chlorine, bromine or iodine.

Alkyl is methyl, ethyl, Isopropyl, n-propyl, n-butyl, isobutyl, sec-butyl, tert-butyl and the various isomeric pentyl, hexyl, heptyl, octyl, nonyl, decyl, undecyl and dodecyl radicals.

Examples of haloalkyl are fluoromethyl, difluoromethyl, trifluoromethyl, chloromethyl, dichloromethyl, trichloromethyl, 2,2,2-trifluorethyl, 2-fluoroethyl, 2-chloroethyl and 2,2,2-trichloroethyl; preferably trichlormethyl, difluorochlormethyl, trifluoromethyl and dichlorofluoromethyl.

Examples of alkoxy are methoxy, ethoxy, propyloxy, isopropyloxy, n-butyloxy, isobutyloxy, s-butyloxy and t-butyloxy; preferably methoxy and ethoxy.

Examples of haloalkoxy are fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, 2-chloroethoxy and trifluoromethoxy.

Examples of cycloalkyl are cyclopropyl, dimethylcyclopropyl, cyclobutyl, cyclopentyl, methylcyclopentyl, cyclohexyl and cycloheptyl, preferably cyclopropyl, cyclopentyl and cyclohexyl.

Examples of alkoxyalkyl are methoxymethyl, ethoxymethyl, propyloxymethyl, methoxyethyl, ethoxyethyl, propyloxyethyl, methoxypropyl, ethoxypropyl and propyloxypropyl.

Examples of halocycloalkyl are 2,2-dichlorocyclopropyl and pentachlorocyclohexyl.

Phenyl, alone or as part of a substituent as in phenoxy, benzyl or benzoyl, can in general be unsubstituted or substituted by further substituents. In this case the substituents can be in the ortho, meta and/or para positions. Preferred substituent positions are the positions ortho and para to the ring linkage site. Preferred substituents are halogen atoms.

Examples of aralkyl are benzyl, phenethyl, 3-phenylpropyl, α-methylbenzyl, phenbutyl and α,α-dimethylbenzyl.

Examples of aryl are phenyl, tetralin, indene, naphthalene, azulene and anthracene.

Examples of heteroaryl are pyrrole, furan, thiophene, oxazole, thiazole, pyridine, pyrazine, pyrimidine, pyridazine, indole, purine, quinoline and isoquinoline.

Examples of heterocycloalkyl are oxirane, oxetane, azetidine, azirine, 1,2-oxathiolane, pyrazoline, pyrrolidine, piperidine, piperazine, morpholine, dioxolane, tetrahydropyran, tetrahydrofuran and tetrahydrothiophene.

The reaction according to the invention is preferably carried out in the liquid phase, in particular using a pulverulent catalyst, either continuously or batchwise as a liquid-phase hydrogenation or in a bubble column or using a formed catalyst in a trickle bed. The reaction can also be carried out in the gas phase using a pulverulent catalyst in a fluidized bed or using a formed catalyst in a fixed bed.

The invention additionally provides for the use of a modified platinum noble metal catalyst, which is modified with a metal selected from the group consisting of lead, mercury, bismuth, germanium, cadmium, arsenic, antimony, silver and gold, for the preparation of aromatic amino compounds which contain at least one —CN group having a multiple bond, or a carbonyl group, on the aromatic radical or in a side chain, by catalytic hydrogenation of corresponding aromatic nitro compounds.

The process according to the invention is particularly suitable for the preparation of aromatic amino compounds which are used, for example, as intermediates in the production of pharmaceuticals, agrochemicals, dyes, photographic materials, pigments and polymers. Examples for the preparation of biologically active compounds, for example herbicides or fungicides, are given in EP-A-0 115 828, EP-A-0 076 370 or EP-A-0 110 048. Examples for the production of polyurethane elastomers are given for example in DE-A 20 65 859, while the preparation of antiinflammatory medicaments is disclosed for example in DE-A 35 34 765.

The suitablility of the process according to the invention extends with very particular preference to the preparation of aromatic amino compounds which are used as intermediates for the production of herbicidally active compounds as described, for example, in WO 96/01254.

Amino compounds of this type are important intermediates for the synthesis of dyes and pigments, polymers, agrochemicals and pharmaceutically active compounds. Consequently, their preparation in good yields and in high purity is a subject of great interest, especially as regards production techniques.

The examples which follow serve to illustrate the present invention in more detail.

PREPARATION EXAMPLES

A) Preparation of the Catalyst

Example A1: Preparation of a 5% Pt-1% Pb-$CaC_3$ catalyst:

5 g of a 5% Pt-$CaCO_3$ catalyst are suspended in 20 ml of water and subsequently 2 ml of a lead acetate solution (0,091 g of Pb(OAc)$_2$. 3H$_2$O; corresponding to 1% Pb) are added slowly at room temperature. The mixture is stirred at room temperature for 10 minutes and then its temperature is raised to 80° C. for 40 minutes. The solid product is filtered off, washed with water and dried at a temperature of 80° C. in vacuo to give the catalyst having a composition of 4,87% Pt and 1% Pb.

B) Preparation of Amines

Example B1: Predaration of 4-chloro-3,5-diaminobenzonitrile 9.1 g of 4-chloro-3,5-dinitrobenzonitrile together with 100 ml of ethyl methyl ketone are initially introduced into a stirred autoclave. 40 mg of FeCl$_2$.4 H$_2$O and 0.18 g of the catalyst from Example A1 are added to the solution. Hydrogenation is carried out at 120° C. and a hydrogen pressure of 20×10⁵ pascals. When hydrogenation is complete the mixture is cooled to room temperature, the reactor is rendered inert with nitrogen and the catalyst is filtered off. The solvent is removed by distillation to give 7 g of crude product having a 4-chloro-3,5-diaminobenzonitrile content of 93.2% and a yield of 97.4%. These figures are determined by gas chromatography.

¹H-NMR: (CDCl₃, 250 MHz) 6.42 ppm (s, 2H); 4.17 ppm (s, broad, 2H).

Example B2: Preparation of 2-chloro-5-aminobenzonitrile 9.22 g of 2-chloro-5-nitrobenzonitrile together with 100 ml of ethyl methyl ketone are initially introduced into a stirred autoclave. 50 mg of FeCl₂.4 H₂O and 0.18 g of the catalyst from Example A1 are added to the solution. Hydrogenation is carried out at 120° C. and a hydrogen pressure of 20×10⁵ pascals. When hydrogenation is complete (1.5 hours) the mixture is cooled to room temperature, the reactor is rendered inert with nitrogen and the catalyst is filtered off. The solvent is removed by distillation to give 7.6 g of crude product having a 2-chloro-5-aminobenzonitrile content of 99.3% and a yield of 98.6%. These figures are determined by gas chromatography.

¹H-NMR: (CDCl₃, 250 MHz) 3.93 ppm (s, broad, 2H); 6.82 ppm (m, 1H); 6.9 ppm (s, 1H); 7.24 ppm (m, 1H).

Example B3: Preparation of 4-aminobenzaldoxime 8.3 g of 4-nitrobenzaldoxime together with 100 ml of tetrahydrofuran are initially introduced into a stirred autoclave. 50 mg of FeCl₂.4 H₂O and 0.2 g of the catalyst from Example A1 are added to the solution. Hydrogenation is carried out at 120° C. and a hydrogen pressure of 20×10⁵ pascals. When hydrogenation is complete, the mixture is cooled to room temperature, the reactor is rendered inert with nitrogen and the catalyst is filtered off. The solvent is distilled off to give, after chromatographic purification, 3.5 g (51% of theory) of 4-aminobenzaldoxime.

¹H-NMR: (d₆-DMSO, 250 MHz) 5.40 ppm (s, 2H); 6.52 ppm (d, 2H); 7.87 ppm (s, 1 H); 10.52 ppm (s, 1H).

Example B4: Preparation of 4-chloro-6-iodo-1.2-phenylenediamine 1.5 g of 4-chloro-2-iodo-6-nitroaniline together with 50 ml of tetrahydrofuran and 10 ml of 1-propanol are initially introduced into a stirred autoclave. 5 mg of FeCl₂.4H₂O and 0.3 g Pt/Pb-CaCO₃ catalyst are added to the solution, and hydrogenation is carried out at 130° C. and 20 bar of hydrogen. After the hydrogenation has come to a standstill, the reaction mixture is cooled to room temperature, the reactor is rendered inert with nitrogen and the catalyst is filtered off. After filtration, the solvent is removed by distillation to give 1.3 g of 4-chloro-6-iodo-1,2-phenylenediamine as a crude product.

¹H-NMR (CDCl₃, 300MHz) 3.56 ppm (s, 2H, broad); 3.77 ppm (s, 2H, broad); 6.68 ppm (s, 1H); 7.18 ppm (s, 1H).

What is claimed is:

1. A process for the preparation of substituted aromatic amino compounds containing at least one unsaturated —CN bond or a carbonyl group on the aromatic radical or in a side chain, by catalytic hydrogenation of aromatic nitro compounds substituted by hydrogenatable or hydrogenolytically eliminable functional groups in the presence of a modified noble metal catalyst, which process comprises the use as noble metal catalyst of platinum which is modified with a metal selected from the group consisting of lead, mercury, bismuth, germanium, cadmium, arsenic, antimony, silver and gold.

2. A process according to claim 1, wherein lead is used as modifying metal.

3. A process according to claim 1, wherein the noble metal catalyst is used in a quantity of from 0.1 to 5% by weight, based on the aromatic nitro compound employed.

4. A process according to claim 1, wherein a noble metal catalyst is used in which the weight ratio of platinum to the modifying metal is from 1:0.001 to 1:1.

5. A process according to claim 4, wherein the weight ratio of platinum to the modifying metal is from 1:0.1 to 1:0.5.

6. A process according to claim 1, wherein a noble metal catalyst is used which contains from 1 to 10% by weight of platinum.

7. A process according to claim 1, wherein a noble metal catalyst is used in which the platinum is present in metallic or oxidized form applied to a support.

8. A process according to claim 7, wherein the support used is active charcoal, silicic acid, silica gel, alumina, calcium carbonate, calcium phosphate, calcium sulfate, barium sulfate, titanium oxide, magnesium oxide, iron oxide, lead oxide, lead sulfate or lead carbonate.

9. A process according to claim 8, wherein the support used is silica gel, alumina or calcium carbonate.

10. A process according to claim 1, wherein a noble metal catalyst is used which contains as promoter a compound of iron, ruthenium, cobalt, copper or manganese.

11. A process according to claim 10, wherein the promoter is used in a quantity of from 0.001 to 10% by weight, based on the aromatic nitro compound employed.

12. A process according to claim 10, wherein the promoter used is an iron salt.

13. A process according to claim 12, wherein the iron salt used is FeCl₂.4H₂O.

14. A process according to claim 1, wherein a noble metal catalyst is used which contains as co-promoters ion pairs or salts which are soluble in organic solvents.

15. A process according to claim 14, wherein in the salts and ion pairs used the cation is $(C_1-C_6 alkyl)_4 N^+$ or

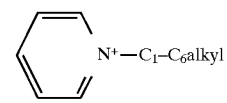

and the anion is Cl⁻, Br⁻, F⁻, BF₄⁻, PF₆⁻, NO₃⁻, F₃CSO₃⁻, BPh₄⁻, PhCOO⁻,

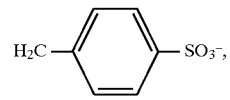

CH₃SO₃⁻ or F₃COO⁻.

16. A process according to claim 14, wherein the co-promoters used are quaternary ammonium bases.

17. A process according to claim 16, wherein tetramethylammonium chloride is used as quaternary ammonium base.

18. Process according to claim 14, wherein the co-promoters are used in a quantity of from 0.001 to 10% by weight, based on the aromatic nitrogen compound employed.

19. A process according to claim 1, which is carried out at a pressure of from 1 to 100 bar and a temperature of from +20° to +160° C.

20. A process according to claim 1, wherein the unsaturated —CN bond is selected from the group consisting of nitrile, oximino, hydrazone, or imine groups, and wherein said unsaturated —CN groups or said carbonyl groups are attached directly to the nitroaromatic radical.

21. A process according to claim 1, wherein the unsaturated —CN bond is selected from the group consisting of nitrile, oximino, hydrazone, or imine groups, and wherein said unsaturated —CN groups or said carbonyl groups are attached in a side chain.

22. A process according to claim 1, wherein the nitroaromatic radical is additionally substituted by at least one halogen atom on the nitroaromatic radical or in a side chain.

23. A process according to claim 1, wherein the compounds are those of the formula I

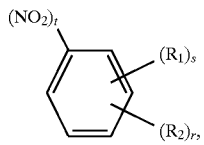

in which
R$_1$ is a group containing at least one —CN unsaturated bond or carbonyl function;
R$_2$ is hydrogen, halogen, C$_1$–C$_{12}$alkyl, C$_1$–C$_{12}$haloalkyl, C$_1$–C$_4$alkyl substituted by phenyl, halophenyl, C$_1$–C$_4$alkylphenyl, C$_1$–C$_4$alkoxyphenyl, halo-C$_1$–C$_4$alkylphenyl, halo-C$_1$–C$_4$alkoxyphenyl, C$_1$–C$_{12}$hydroxyalkyl, C$_3$–C$_8$cycloalkyl, C$_6$–C$_{16}$aryl, C$_7$–C$_{16}$aralkyl, C$_3$–C$_6$heterocycloalkyl, C$_3$–C$_{16}$heteroaryl, C$_4$–C$_{16}$heteroaralkyl, X$_1$R$_3$, where R$_3$ is hydrogen, C$_1$–C$_{12}$alkyl, C$_1$–C$_{12}$haloalkyl, C$_1$–C$_4$alkyl substituted by phenyl, halophenyl, C$_1$–C$_4$alkylphenyl, C$_1$–C$_4$alkoxyphenyl, halo-C$_1$–C$_4$alkylphenyl, halo-C$_1$–C$_4$alkoxyphenyl, C$_1$–C$_{12}$hydroxyalkyl, C$_3$–C$_8$cycloalkyl, C$_6$–C$_{16}$aryl, C$_7$–C$_{16}$aralkyl, C$_3$–C$_6$heterocycloalkyl, C$_3$–C$_{16}$heteroaryl or C$_4$–C$_{16}$heteroaralkyl, X$_1$ is oxygen or sulfur;

r, s and t are 1, 2 or 3, and r+s+t is less than or equal to 6.

24. A process according to claim 23, wherein in the formula I r, s and t are 1 or 2.

25. A process according to claim 23, wherein R$_1$ is a group Q—CN, Q—C=N—R$_4$ or Q—COR$_5$, where R$_4$ is OH, O—(C$_1$–C$_{12}$)alkyl, NHCO(C$_1$–C$_{12}$)alkyl or NHCO phenyl, R$_5$ is C$_1$–C$_{12}$alkyl, O—C$_1$–C$_{12}$alkyl or O—N=C[(C$_1$–C$_{12}$)alkyl]$_2$ and Q is either a direct bond or an unsubstituted or additionally halogen- or C$_1$–C$_4$alkyl-substituted pyrazolyl, pyrimidyl, or pyrimidyldione radical.

26. A process according to claim 23, wherein in the compound of the formula I R$_2$ is hydrogen, halogen, C$_1$–C$_6$alkyl, C$_1$–C$_6$haloalkyl or C$_1$–C$_6$haloalkoxy.

27. A process according to claim 26, wherein R$_2$ is hydrogen, halogen, methyl, difluoromethoxy or trifluoromethoxy.

28. A process according to claim 23, wherein Q is a direct bond and R$_1$ is a nitrile group or —C=N—OR$_4$;
R$_2$ is halogen and r, s and t are each 1 or 2, where
R$_4$ is OH, O—C$_1$–C$_{12}$alkyl, NHCO(C$_1$–C$_{12}$)alkyl or NHCO phenyl.

29. A process according to claim 23, wherein Q is a direct bond and R$_1$ is COH or CO(C$_1$–C$_{12}$)alkyl.

* * * * *

UNITED STATES PATENT AND TRADEMARK OFFICE
CERTIFICATE OF CORRECTION

PATENT NO. : 5,877,340
DATED : March 2, 1999
INVENTOR(S) : Peter Baumeister, Urs Siegrist It is certified that error appears in the above-identified patent and that said Letters Patent is hereby corrected as shown below:

Column 8, line 45, please delete

"$H_2C$" and substitute therefor -- $H_3C$ --.

Column 9, line 15, please delete

"-CN unsaturated" and substitute therefor -- unsaturated -CN --

Signed and Sealed this

Twenty-ninth Day of June, 1999

Attest:

Q. TODD DICKINSON

*Attesting Officer*  Acting Commissioner of Patents and Trademarks